June 19, 1973 A. P. J. DE BEER Plant Pat. 3,361
CONIFER PLANT
Filed July 1, 1971
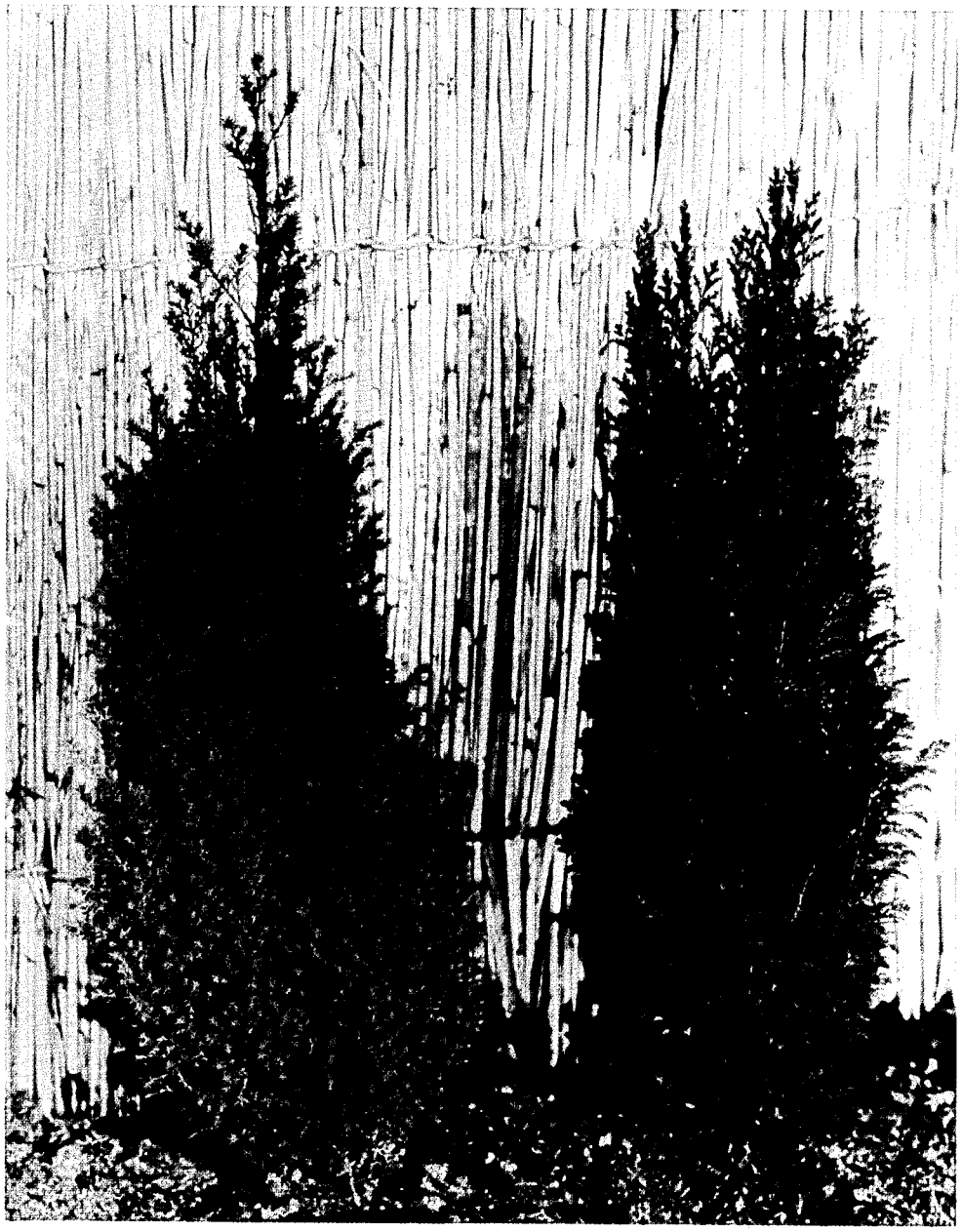

United States Patent Office

Plant Pat. 3,361
Patented June 19, 1973

3,361
CONIFER PLANT

Antonius Petrus Johannes de Beer, Bosscheweg 165, Tilburg, Netherlands

Filed July 1, 1971, Ser. No. 159,071
Int. Cl. A01h *5/00*
U.S. Cl. Plt.—50 1 Claim

ABSTRACT OF THE DISCLOSURE

A new and distinct variety of conifer obtained as a cultivated seeedling, derived from seeds of an unidentified and unpatented *Chamaecyparis lawsoniana* genus.

SUMMARY OF THE INVENTION

The present discovery relates to a new and distinct variety of ornamental conifer of the *Chamaecyparis lawsoniana* genus, which originated as a selected cultivated seedling derived from seeds of an unidentified and unpatented *Chamaecyparis lawsoniana* tree.

This new variety is by its compact form and its attractive bluish-grey color particularly useful and desirable for parks and private gardens. The novelty and distinctiveness of my new *Chamaecyparis lawsoniana* tree are evident by the following outstanding characteristics, which differentiate it from the common species *Chamaecyparis lawsoniana* as well as from all other varieties:

(1) A distinctive bluish-grey color of the leaves, which persists throughout the year.

(2) The plant is winter hardy in temperate zone (till −30° C.).

(3) The habit of growth is very compact and cone-shaped in an outstanding way, different from all other varieties.

(4) In the first three or four years, the plant remains small and compact; later the growth is more vigorous, but the plant remains compact.

(5) The branches and branchlets are extremely numerous, ascending; the leaves are decussate.

BRIEF DESCRIPTION OF DRAWINGS

The accompanying drawing shows typical specimens of my new variety of conifer, the foliate of which is depicted in color as nearly true as is possible to make the same in a color illustration of this character and wherein the view of the new variety on the left side is compared with the standard *Chamaecyparis lawsoniana* three on the right.

DETAILED DESCRIPTION OF VARIETY

The new conifer was discovered as a seedling derived from seeds of an unidentified and unpatented *Chamaecyparis lawsoniana* tree. The seeds were sown and grown by me on cultivated property under my special control and supervision in my nursery fields in Tilburg, Netherlands.

The original seeds resulted from open pollination of the parent tree and the seedling derived therefrom were carefully selected by me and ultimately confirmed to the single seedling which I selected because of its precious and unique combination of characteristics never previously exhibited in a *Chamaecyparis lawsoniana* tree of which I am aware.

The bluish-grey color is the color as identified by number 00858/1 (Leekgreen) page 197, freshened by the more vivid color 00058/1, page 194, of the "Equivalent to British Color Council, Ridway Repertoire Ostwald."

Growth: Compact, conical, ascending, the branchlets are ascending, very ramified.

The length of the leaves is from 3 to 6 mm. and the breadth 0.75 to 1.5 mm.; the leaves are needle forming decussate, more sharply pointed than of other forms and varieties of the species.

This variety has a dense, conical habit with upright, heavily branched stems. The leaves are needle-like (not scale-like as in many other lawsoniana cultivars), decussate (alternating in pairs at right angles), 3–6(–9) mm. long, 0.75–1.5 mm. wide, thin and rather sharply pointed, conspicuously glue-grey.

This variety has a color of leaves much deeper blue than other known comparable varieties of cultivars, with a vigorous growth, and yet compact.

Asexual reproduction by cuttings as performed by me at my nursery at Tilburg, Netherlands, shows that all the foregoing characteristics and distinctions come true and are established and transmitted through succeeding propagations.

The accompanying drawing in full color shows a view of a three year old plant species in comparison with a three year old plant of the "normal" form of the species. A three year old plant attained a height of approximately 50 cm.

I claim:

1. A new and distinct variety of conifer discovered as a seedling from seeds of a *Chamaecyparis lawsoniana* tree characterized particularly by its distinctive bluish color of the needle-like leaves which persists throughout the year, the compact and cone-shaped habit of growth and by the numerous ascending branches, substantially as shown and described.

No references cited.

ROBERT E. BAGWILL, Primary Examiner